United States Patent

Oohashi et al.

Patent Number: 5,859,048
Date of Patent: Jan. 12, 1999

[54] PHARMACEUTICS FOR MUCOSAL ADMINISTRATION

[75] Inventors: Masami Oohashi, Inagi; Noriaki Uchida, Kawasaki; Junichi Sakata, Machida; Masaru Sunamoto, Sagamihara, all of Japan

[73] Assignee: Teikoku Hormone MFG. Co., Ltd., Tokyo, Japan

[21] Appl. No.: 860,459

[22] PCT Filed: Dec. 22, 1997

[86] PCT No.: PCT/JP95/02633

§ 371 Date: Jun. 25, 1997

§ 102(e) Date: Jun. 25, 1997

[87] PCT Pub. No.: WO96/20001

PCT Pub. Date: Jul. 4, 1996

[30] Foreign Application Priority Data

Dec. 28, 1994 [JP] Japan ................................. 6-340372
Dec. 28, 1994 [JP] Japan ................................. 6-340381

[51] Int. Cl.⁶ .................................................. A01N 43/36
[52] U.S. Cl. .......................... 514/428; 514/2; 514/427; 424/433
[58] Field of Search ............................. 514/2, 427, 428; 424/433

[56] References Cited

U.S. PATENT DOCUMENTS

| | | | |
|---|---|---|---|
| 4,434,159 | 2/1984 | Sekine et al. | 424/178 |
| 4,485,033 | 11/1984 | Kitao et al. | 252/315.4 |
| 4,952,560 | 8/1990 | Kigsawa et al. | 514/2 |
| 5,238,917 | 8/1993 | Fuji et al. | 514/2 |

FOREIGN PATENT DOCUMENTS

| | | |
|---|---|---|
| 0533938 | 3/1993 | European Pat. Off. |
| 56-122310 | 9/1981 | Japan |
| 63-35 | 1/1987 | Japan |
| 1-313419 | 12/1989 | Japan |
| 4-149126 | 5/1992 | Japan |
| WO 92/14479 | 3/1992 | WIPO |

Primary Examiner—Marianne M. Cintins
Assistant Examiner—Dwayne C. Jones
Attorney, Agent, or Firm—Wenderoth, Lind & Ponack, L.L.P.

[57] ABSTRACT

In pharmaceutics for mucosal administration containing pharmacologically active peptides or proteins and tolmetin or salts thereof exhibited very excellent effect as mucosal absorption enhancers.

Furthermore, when the pharmaceutics for mucosal administration are for rectal administration, the suppository in which at least either the active ingredient, peptide or protein, or the mucosal absorption enhancer is converted to a complex with a high molecular compound dissolving in water at pH 5 or higher and together uniformly dispersed in a fatty suppository base exhibited markedly improved rectal absorbability compared with that of conventional pharmaceutics for rectal administration and at the same time increased stability of the peptide or protein which is the active ingredient.

12 Claims, 2 Drawing Sheets

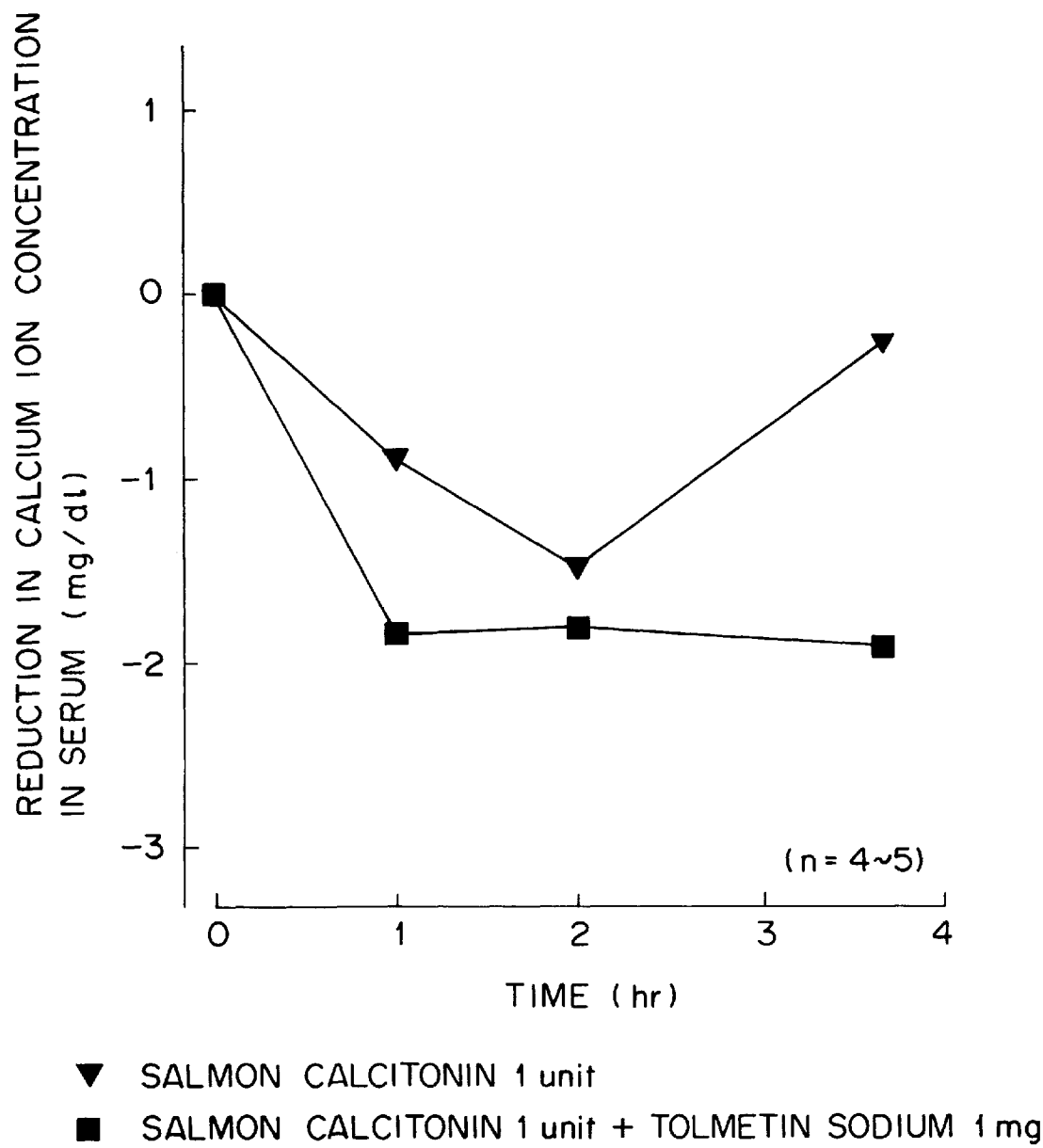

PHARMACEUTICS FOR MUCOSAL ADMINISTRATION

BACKGROUND OF THE INVENTION

1. Field of the Invention

This invention relates to pharmaceutics for mucosal administration of pharmacologically active peptides or proteins, which exhibit excellent mucosal absorbability.

2. Description of the Related Art

Administration of pharmacologically active peptides or proteins has heretofore been normally effected by injection means, for the reasons that oral administration results in poor drug absorption and their decomposition and deactivation in the digestive tract. However, administration by injection is painful and involves risks of inducing amyotrophia (muscle atrophy) or other diseases. There is also a problem of inconvenience for the patients who need to attend hospitals to be injected.

In the recent years, a variety of methods for administering peptides or proteins to replace injections are being tried, such as the administration to the rectum, vagina, nasal or oral mucosa. These mucosal administration means have the advantages of preventing deactivation of the drug and avoiding side effects such as digestive tract disorder which accompany oral administration. Generally, however, peptides or proteins show very poor mucosal absorbability and hence ordinary pharmaceutics for mucosal administration have the defect of failing to provide satisfactory high drug concentration in blood to exhibit the expected pharmaceutical efficacy.

Hence, various absorption enhancers to promote mucosal absorption of peptides or proteins have been studied and proposed. As organic acid type absorption enhancers, for example, salicylic acid or derivatives thereof [KOKAI Patent Application Sho 56(1981)-122310(A) JP], acidic amino acid or derivatives thereof [KOKAI Patent Application Sho 56(1981)-138115(A) JP] and capric acid or salts thereof [KOKAI Patent Application Sho 62(1987)-35(A) JP] are known. However, these mucosal absorption enhancers have the problems of being irritative to the mucosae and exhibiting yet insufficient mucosal absorption enhancing effect. Thus they are not fully satisfactory as mucosal absorption enhancers for peptides or proteins.

Furthermore, most of the pharmaceutics for rectal administration (which may be hereafter referred to as "suppository"), which is a form of mucosal administration, are formulated following the ordinary practice of uniformly dispersing and blending the drug as incorporated with an absorption enhancer in and with a suppository base. However, peptides or proteins are apt to cause such formulative problems when the ordinary method is adopted, as becoming unstable under the influences of absorption enhancer or suppository base or failing to provide a sufficient dose of rectal absorption because of insufficient release ability after administration. Thus, satisfactory pharmaceutics for rectal administration of the peptides or proteins have not yet been obtained.

Whereas, Kokai Patent Application Hei 1(1989)-313419 (A) JP discloses a pharmaceutic for rectal administration in which a solid composed of the pharmacologically active ingredient and water-soluble macromolecules is uniformly dispersed in a fatty suppository base. The function and effect of the invention as disclosed in said Kokai Gazette, however, are to secure stable and good release of a pharmaceutically effective ingredient from the pharmaceutic irrelevantly to physical properties of the effective ingredient or those of the fatty suppository base. Hence the Gazette simply discloses the use of non-pH-dependent water-soluble macromolecules such as polyvinylpyrrolidone, macrogoal, and the like, stating nothing about promotion of rectal absorption of pharmaceutically active ingredient.

An object of the present invention is to provide pharmaceutics for mucosal administration exhibiting still improved mucosal absorption of pharmacologically active peptides or proteins.

Another object of the invention is to provide stable pharmaceutics for rectal administration exhibiting further improved rectal absorption of pharmacologically active peptides or proteins.

SUMMARY OF THE INVENTION

We have engaged in extensive studies on pharmaceutics containing pharmacologically active peptides or proteins for mucosal administration to find tolmetin or salts thereof are very excellent mucosal absorption enhancers.

We furthermore found that pharmaceutics for rectal administration, in which at least either of the pharmacologically active ingredient or the mucosal absorption enhancer is caused to form a complex with a high molecular compound which is soluble in water at pH 5 or higher and these components are uniformly dispersed in fatty suppository base, exhibit markedly improved rectal absorption compared with that of conventional pharmaceutics for rectal administration and increased stability of peptides or proteins which are the active ingredient.

According to an embodiment of the present invention, pharmaceutics for mucosal administration (hereafter referred to as "pharmaceutics I") which are characterized by containing (A) pharmacologically active peptides or proteins and tolmetin or salts thereof are provided.

According to another embodiment of the present invention, pharmaceutics for rectal administration containing (A) pharmacologically active peptides or proteins and (B) mucosal absorption enhancers are provided, which are characterized in that at least either of said (A) effective component (a peptide or protein) or (B) said mucosal absorption enhancer is caused to form a complex with (C) a high molecular compound which dissolves in water at pH 5 or higher, and that both the (A) peptides or proteins and (B) mucosal absorption enhancer are uniformly dispersed in fatty suppository base (the pharmaceutics are hereafter referred to as "pharmaceutics II").

Furthermore, as a preferred embodiment of said pharmaceutics II of the present invention, pharmaceutics for rectal administration are provided, in which both (A) a pharmacologically active peptide or protein and (B) mucosal absorption enhancer are converted to complexes with (C) a high molecular compound dissolving in water at pH 5 or higher, and are uniformly dispersed in a fatty suppository base.

BRIEF DESCRIPTION OF THE DRAWINGS

FIG. 2 is a graph showing the result of an intranasal administration test with rats of salmon calcitonin in the form of a collunarium as obtained in Example 4.

DETAILED DESCRIPTION OF THE INVENTION

Figure 1:
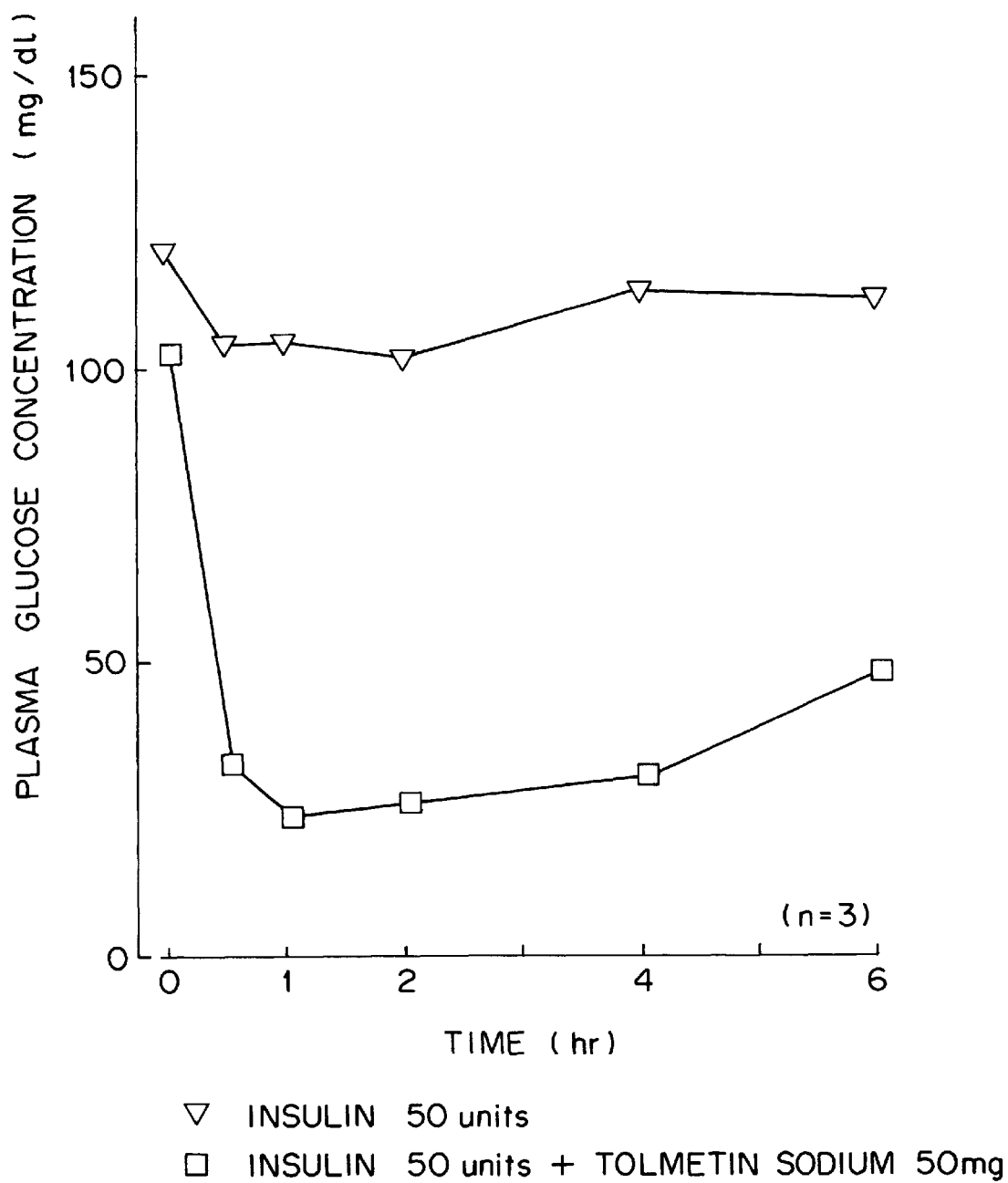
FIG. 1 is a graph showing the result of a rectal absorption test with rabbits of insulin in the form of suppository as obtained in Example 3.

As (A) pharmacologically active peptides or proteins which are useful for the pharmaceutics I and II of the present invention, for example, calcitonin, insulin, glucagon, gastrin, oxytocin, angiotensin, vasopresin, felypressin, gonadotropic hormone-releasing hormone, corticotropin, prolactin, somatotropin, thyrotropin, kallikrein, parathyrin, secretin, gonadotropin, somatostatin, interferon, enkephalin and endorphin can be named. In particular, calcitonin, oxytocin, insulin and vasopresin are preferred.

Tolmetin which is used as the mucosal absorption enhancer in the pharmaceutics I is a common name of a compound of a chemical name 1-methyl-5-(4-methylbenzoyl)-1H-pyrrole-2-acetic acid. As salts of tolmetin, for example, inorganic salts such as sodium salts, potassium salts, lithium salts, magnesium salts, aluminum salts and iron salts; and organic amine salts such as ammonium salts may be named. Among those, sodium salts are preferred.

The pharmaceutics I for mucosal administration of the present invention can be formulated, according to their administration routes, into those for rectal administration (suppository), those for vaginal administration (vaginal suppository or pessary), those for intranasal administration (collunarium) and those for oral mucosal administration. Of those, suppository or collunarium, inter alia, suppository pharmaceutics are preferred.

These pharmaceutics can be made by formulating above-described pharmacologically active peptide or protein and tolumetin or salt thereof, concurrently with adjuvants which are normally used in those pharmaceutics, by a method known per se.

As examples of additives (base) for, eg, suppository, the following can be named: semi-synthetic hard fat such as Isocacao® (Kao Corp.), Witepsol® (Hüls), Suppocire® (Gattefossé), Pharmasol® (NOF Corp.), Massa Estarinum® (Hüls), Novata® (Henkel) and SB base (Taiyo Yushi); natural oil such as cacao butter, palm oil, palm kernel oil, coconut oil, fractional coconut oil and lard; waxes such as lanolin and reduced lanolin; hydrocarbons such as vaselin, squalene, squalane and liquid paraffin; higher alcohols such as lauryl alcohol, cetanol and stearyl alcohol; fatty acid esters such as butyl stearate and dilauryl malonate; glycerin medium and long chain carboxylic acid esters such as triolein and tristearin; glycerin-substituted carboxylic acid esters such as glycerin acetoacetic acid ester; and polyethylene glycols and derivatives thereof such as macrogol and cetomacrogol.

As examples of useful additives when the pharmaceutics are in the form of collunarium, the following may be used: buffering agents of butyrate type, acetate type and phosphate type; physiological saline water; fungicide and antiseptics such as p-oxybenzoic acid ester, propylene glycol, benzethonium chloride, benzalkonium chloride, sorbic acid and salts thereof, and chlorobutanol; thickeners such as polyvinyl alcohol, polyvinyl pyrrolidone, dextran, metal salts of alginic acid, sucrose, gelatine, methyl cellulose and metal salts of hyaluronic acid; and powder base such as crystalline cellulose, α-cellulose, crosslinked carboxymethyl cellulose sodium, hydroxypropyl cellulose, β-cyclodextrin, dimethyl-β-cyclodextrin and lactose.

In the pharmaceutics I of the present invention, tolmetin or a salt thereof as the absorption enhancer is normally added at a ratio of 0.01–50% by weight, preferably about 5–20% by weight to the total amount of the pharmaceutic. Again, tolmetin or a salt thereof can be used normally at a ratio in the order of 100–50,000 parts by weight, preferably 500–10,000 parts by weight, per 1 part by weight of a pharmacologically active peptide or protein.

Whereas, as (C) the high molecular compounds which dissolve in water at pH 5 or higher and are to be used in the pharmaceutics II of the present invention, for example, methacrylic acid copolymer L (Eudragit® L100-55), carboxymethylethyl cellulose, hydroxypropylmethyl cellulose phthalate and hydroxypropylmethyl cellulose acetate succinate may be named.

As useful (B) mucosal absorption enhancer, for example, the following may be named besides aforesaid tolmetin or salts thereof: capric acid, sodium caprate, salicylic acid, sodium salicylate, acetylsalicylic acid, benzilic acid, taurocholic acid and sodium taurocholate. Of those, tolmetin and salts thereof, sodium caprate and benzilic acid are conveniently used.

As the fatty suppository base in the pharmaceutics II of the present invention, any of fatty suppository bases normally useful for pharmaceutics for rectal administration can be used. More specifically, those semi-synthetic hard fats and natural oils as previously named may be used.

A complex of (A) a peptide or protein with (C) a high molecular compound which is water-soluble at pH 5 or higher, to be present in the pharmaceutics II can be prepared by dissolving or dispersing powders of (A) and (C) in an organic solvent such as acetone, acetone/water mixture, ethanol, ethanol/water mixture, ethanol/dichloromethane mixture, ethanol/dichloromethane/water mixture or the like, and removing the solvent from the resultant solution or suspension by such means as spray drying, fluidized bed drying or drying under reduced pressure.

The ratio of use of (A) a peptide or protein and (C) a high molecular compound, which dissolves in water at pH 5 or higher, forming a complex is not subject to a critical limitation but is suitably variable depending on the kinds of peptide or protein and the water-soluble high molecular compound, while they can generally be used at (A):(C) by weight of 1:1 to 1:30,000, preferably around 1:10 to 1:1,000.

A complex of (B) a mucosal absorption enhancer and (C) a high molecular compound dissolving in water at pH 5 or higher can also be prepared in the manner similar to the preparation of above complex of (A) peptide or protein with (C) a high molecular compound dissolving in water at pH 5 or higher.

The use ratio of (B) a mucosal absorption enhancer and (C) a high molecular compound dissolving in water at pH 5 or higher again is not strictly limited, but differs depending on, for example, the amount of the mucosal absorption enhancer used. Whereas, they can be generally used at (B):(C) by weight of 1:0.1 to 1:1,000, preferably about 1:0.1 to 1:10.

The pharmaceutics II of the present invention can be prepared by mixing into a molten fatty suppository base said components (A) and (B) at lease one of which has been converted to a complex, and stirring the mixture under gradual cooling whereby uniformly dispersing the components (A) and (B) at least one of which is in a complex form in the base; and pouring the resulting pasty mixture into a suppository container with stirring. The use ratio of the component (A) to component (B) in that occasion is, in terms of a weight ratio of (A):(B) in the state not yet converted to the complex(s), generally 1:100–1:50,000, preferably around 1:500–1:10,000.

The blend ratio of these components into the fatty suppository base is subject to no critical limitation. Whereas, from the standpoint of their dispersibility in the base and moldability of the pharmaceutic, the sum of the components (A) and (B) at least one of which is used in the form of a complex, may generally range around 1–50% by weight, preferably around 5–20% by weight, based on the total amount of the pharmaceutic.

The pharmaceutics II of the present invention may contain such adjuvants which have been normally used in this kind of pharmaceutics as surfactants, preservatives, coloring agents, stabilizers and pH-regulants.

Above-described pharmaceutics I and II of the present invention exhibit excellent characteristics of markedly improved mucosal absorbability over that of conventional pharmaceutics for mucosal administration. The pharmaceutics II, furthermore, are stable under a prolonged storage.

EXAMPLES

Hereafter the present invention is still more specifically explained, referring to working Examples.

Example 1

9.49 Grams of lsocacao® (Kao Corporation) was melted on an aqueous bath at about 50° C. and mixed with 500 mg of tolmetin sodium which had been finely pulverized with a jet mill. The mixture was withdrawn from the aqueous bath and gradually cooled under stirring. When the mixture came to have an adequate temperature and viscosity, 10 mg of a lyophilized powder of salmon calcitonin (S-CT: S-CT content of the lyophilized powder was 1% by weight) was added and stirred vigorously for uniform dispersion. The resultant paste was poured into a suppository container under stirring. Thus a 1 g of suppository was obtained (S-CT content: 50 units and tolmetin sodium content: 50 mg, per capsule).

A rectal absorption test with rabbits was conduced as follows. Three Japanese white male rabbits (body weight: 2.8–3.8 kg) per group, which fasted for two days before the test were used. After inserting the pharmaceutics for rectal administration as obtained in this Example into the rectal of the rabbits, their anul parts were fastened with clips to prevent the drug from leakage. Blood was drawn from the rabbits via ear vein at regular time intervals by about 1.5 ml per rabbit per drawing, and the S-CT concentration in each serum was measured by radioimmunoassay. The results were as shown in Table 1.

The test results are expressed by the maximum S-CT concentration in the serum (C max) and the area under the blood concentration-time curve (AUC). As comparative examples, the results of C max and AUC measurements of suppositories prepared in the identical manner with above, except that tolmetin sodium as the absorption enhancer was replaced by sodium caprate, acetylsalicylic acid, and sodium salicylate, respectively, are concurrently presented.

TABLE 1

| Absorption enhancer | C max (ng/ml) | AUC (ng · hr/ml) |
|---|---|---|
| Present invention | | |
| (tolmetin sodium) | 2.09 | 0.98 |
| Comparative examples | | |
| (sodium caprate) | 1.50 | 0.76 |
| (acetylsalicylic acid) | 1.13 | 0.47 |
| (sodium salicylate) | 0.42 | 0.14 |
| (no absorption enhancer added) | 0.07 | 0.03 |

Example 2

The procedures of Example 1 were repeated except that S-CT as the peptide was replaced by 20 mg of lyophilized oxytocin powder (containing 0.77% by weight of oxytocin), to provide 1 g of suppository (containing 10 units of oxytocin and 50 mg of tolmetin sodium per capsule).

This was administered to rabbits similarly to Example 1, their blood was drawn and plasmic oxytocin concentration was measured by radioimmunoassay. The results were as shown in Table 2. As comparative examples, measured results of C max and AUC of the same suppository not containing any absorption enhancer are concurrently presented.

TABLE 2

| Absorption enhancer | C max ($\mu$U/ml) | AUC ($\mu$U · /hr/ml) |
|---|---|---|
| Present invention | | |
| (tolmetin sodium) | 1346.67 | 828.39 |
| Comparative example | | |
| (No absorption enhancer added) | N.D. | N.D. |

N.D. signifies that the values were less than the detection limit of 3.0 $\mu$l/ml.

Example 3

The procedures of Example 1 were repeated except that 20 mg of insulin was used as the peptide, instead of S-CT, to provide 1 g of suppository (containing 50 units of insulin and 50 mg of tolmetin sodium per capsule).

The results of rectal absorption test with rabbits using the above-obtained suppository were as illustrated in FIG. 1. The rectal absorbability of insulin was evaluated by variation in plasmic glucose concentration.

As a comparative example, the variation in plasmic glucose concentration as measured using the suppository not containing any absorption enhancer is concurrently presented.

Example 4

One (1) mg of S-CT was dissolved in 500 $\mu$l of physiological saline water, to form a S-CT undiluted solution of 10000 (i $\mu$/ml). Twenty (20) $\mu$l of this undiluted solution and 200 mg of tolmetin sodium were taken into a 10 ml-volumetric flask and a balance amount of physiological saline water was added to make the solution exactly 10 ml to provide a collunarium (containing 1 unit of S-CT and 1 mg of tolmetin sodium, per 50 $\mu$l of the pharmaceutic).

An intranasal absorption test with rats was conducted following the method of Hirai, et al. (*J Pharm. Sci.*, Vol. 69, 1411 (1980)).

That is, to 4 to 5 rats per group the above collunarium was administered through polyethylene tube inserted into the rats' nasal cavities, at a dose of 1 unit of S-CT per rat. The rats' blood was drawn before the administration and at 0.5, 1, 2 and 4 hours after the administration and calcium ion concentration values in their blood sera were measured with atomic spectrophotometry. The results were as shown in FIG. 2.

As a comparative example, the results of measuring seramic calcium ion concentration using the same collunarium containing no absorption enhancer are concurrently presented.

Example 5

Ten (10) mg of salmon calcitonin (S-CT) and 10 g of Eudragit® L100-55 (Röhm Pharma GMBH WEITERSTADT) were dissolved in 500 ml of ethanol/dichloromethane/water mixed liquid (49:49:2) and the solution was spray dried to provide a S-CT-Eudragit L100-55 complex.

Separately, 10 g of tolmetin sodium and 10 g of Eudragit L100-55 were dissolved in 500 ml of ethanol/dichloromethane/water mixed liquid (45:45:10) and the solution was spray dried to provide a tolmetin sodium-Eudragit L100-55 complex.

Isocacao® (Kao Corp.) 8.9 g was melted on an aqueous bath at about 50° C., and blended with 1 g of said tolmetin sodium-Eudragit L100-55 complex.

The mixture was withdrawn from the aqueous bath and gradually cooled under stirring. At a stage when the temperature and viscosity of the mixture became appropriate, 100 mg of said S-CT-Eudragit L100-55 complex was added and uniformly dispersed under vigorous stirring. The resulting paste was poured into a suppository container under stirring to provide 1 g of suppository (containing 50 units of S-CT and 50 mg of tolmetin sodium per capsule).

A rectal absorption test with rabbits was conducted, in which 2 to 3 Japanese white male rabbits (body weight 2.8–3.8 kg each) per group were used, which were fasted for two days preceding the test. After inserting the suppository as obtained in this Example into the rectus of each test rabbit, its anus part was fastened with a clip to prevent the drug from leakage. Blood was drawn from each test rabbit via the ear vein at regular time intervals, by about 1.5 ml per drawing, and the S-CT concentration in the blood serum was measured by radioimmunoassay. The results were: the maximum S-CT concentration in the serum (C max) was 4.38 ng/ml and the area under the blood concentration-time curve (AUC) was 2.00 ng.hr/ml.

Example 6

9.4 Grams of Massa Estarinum® 299 (Huls) was melted on an aqueous bath at about 50° C., and into which 500 mg of tolmetin sodium was added and blended. The mixture was withdrawn from the aqueous bath and gradually cooled under stirring. When the mixture came to have an adequate temperature and viscosity, 100 mg of the S-CT-Eudragit L100-55 complex as obtained in Example 5 was added and uniformly dispersed under vigorous stirring. The resulting paste was poured into a suppository container under stirring to provide 1 g of a suppository (containing 50 units of S-CT and 50 mg of tolmetin sodium per capsule).

The results of rectal absorption test of this suppository using rabbits were: C max was 2.88 ng/ml and AUG was 1.51 ng.hr/ml.

Example 7

9.0 Grams of Massa Estarinum® 299 (Huls) was melted on an aqueous bath at about 50° C., which was blended with 1 g of the tolmetin sodium-Eudragit L100-55 complex as obtained in Example 5. The mixture was withdrawn from the aqueous bath and gradually cooled under stirring until it came to have adequate temperature and viscosity. Whereupon 0.1 mg of S-CT was added thereto and uniformly dispersed under vigorous stirring. The resulting paste was poured into a suppository container under stirring to provide 1 g of a suppository (containing 50 units of S-CT and 50 mg of tolmetin sodium per capsule).

The results of the rectal absorption test of this suppository using rabbits were: C max was 2.94 ng/ml and AUG was 1.89 ng.hr/ml.

Example 8

Example 5 was repeated except that 8.9 g of SB-AM (Taiyo Yushi K.K.) was used as a fatty suppository base instead of Isocacao®, to provide 1 g of a suppository (containing 50 units of S-CT and 50 mg of tolmetin sodium per capsule).

The results of the rectal absorption test of this suppository using rabbits were: C max was 3.00 ng/ml and AUG was 2.16 ng.hr/ml.

We claim:

1. Pharmaceutics for mucosal administration characterized by containing (A) pharmacologically active peptide or proteins and tolmetin or a salt thereof as a mucosal absorption enhancer.

2. Pharmaceutics for mucosal administration according to claim 1, in which (A) the pharmacologically active peptide or protein is calcitonin, oxytocin, insulin or vasopresin.

3. Pharmaceutics for mucosal administration according to claim 1, in which the pharmaceutics are in a form suitable for rectal administration, vaginal administration, intranasal administration or oral mucosal administration.

4. Pharmaceutics for mucosal administration according to claim 1, in dosage unit form, wherein the tolmetin or salt thereof is present in an amount, per dosage unit, which exhibits substantially no medicinal efficacy.

5. Pharmaceutics for rectal administration characterized by containing (A) pharmacologically active peptide or protein and (B) a mucosal absorption enhancer, in which at least either of (A) the peptide or protein and (B) the mucosal absorption enhancer has been converted into a form of a complex with (C) a high molecular compound which is water soluble at pH 5 of higher, and both (A) the peptide or protein and (B) the mucosal absorption enhancer are uniformly dispersed in a fatty suppository base.

6. Pharmaceutics for rectal administration according to claim 5, in which both (A) the pharmacologically active peptide or protein and (B) the mucosal absorption enhancer have been converted into complexes with (C) the high molecular compound which is water soluble at pH 5 or higher.

7. Pharmaceutics for rectal administration according to claim 5, in which (A) the pharmacologically active peptide or protein is calcitonin, oxytocin, insulin or vasopresin.

8. Pharmaceutics for rectal administration according to claim 5, in which (B) the mucosal absorption enhancer is tolmetin or a salt thereof, sodium caprate or benzilic acid.

9. Pharmaceutics for rectal administration according to claim 5, in which the weight ratio A:C in the complex of (A) the pharmacologically active peptide or protein and (C) the high molecular compound which is water soluble in water at pH 5 or higher is from 1:1 to 1:30,000.

10. Pharmaceutics for rectal administration according to claim 5, in which the weight ratio (B):(C) in the complex of (B) the mucosal absorption enhancer and (C) the high molecular compound which is water-soluble at pH 5 or higher is from 1:0.1 to 1:1000.

11. Pharmaceutics for rectal administration according to claim 5, wherein (C) the high molecular compound is water-insoluble at a pH lower than 5.

12. Pharmaceutics for rectal administration characterized by containing (A) pharmacologically active peptide or protein and (B) a mucosal absorption enhancer, in which at least either of (A) the peptide or protein and (B) the mucosal absorption enhancer has been converted into a form of a complex with (C) a high molecular compound which is water-soluble at pH 5 or higher, and both (A) the peptide or protein and (B) the mucosal absorption enhancer are uniformly dispersed in a fatty suppository base, and wherein (C) the high molecular compound is methacrylic acid copolymer L, carboxymethylethyl cellulose, hydroxypropylmethyl cellulose phthalate or hydroxypropylmethyl cellulose acetate succinate.

* * * * *